United States Patent [19]

Mehl et al.

[11] 4,300,404
[45] Nov. 17, 1981

[54] LIQUID SPECIMEN CONTAINER

[75] Inventors: Jack J. Mehl, Landing; Cyril J. Calpin, Oak Ridge, both of N.J.

[73] Assignee: Becton, Dickinson and Company, Paramus, N.J.

[21] Appl. No.: 74,019

[22] Filed: Sep. 10, 1979

Related U.S. Application Data

[63] Continuation-in-part of Ser. No. 856,304, Dec. 1, 1977, abandoned.

[51] Int. Cl.³ .............................................. G01N 1/14
[52] U.S. Cl. ............................. 73/863.52; 73/864.52; 73/864.91
[58] Field of Search ...................... 73/425.4 R, 425.6; 128/763, 764

[56] References Cited

U.S. PATENT DOCUMENTS

| | | | |
|---|---|---|---|
| 57,256 | 8/1866 | Meglone | 141/329 |
| 2,953,132 | 9/1960 | Richter | 141/329 |
| 3,066,671 | 12/1962 | Cohen | 128/272 |
| 3,608,550 | 9/1971 | Stawski | 128/272.3 |
| 3,904,482 | 9/1975 | Mehl | 128/2 F |
| 4,024,857 | 9/1971 | Blecher | 128/2 F |
| 4,116,066 | 9/1978 | Mehl et al. | 73/425.6 |

FOREIGN PATENT DOCUMENTS

| | | | |
|---|---|---|---|
| 1227395 | 3/1960 | France | 128/272 |
| 947908 | 1/1964 | United Kingdom | 128/DIG. 5 |
| 1019500 | 2/1966 | United Kingdom | 128/DIG. 5 |

*Primary Examiner*—S. Clement Swisher

[57] ABSTRACT

A liquid collection container and a lid adapted to fit over the container, said lid having a cannula which extends into the lower end of the container and which projects through the lid at its upper end so as to be able to pierce the stopper of an air-evacuated, tubular container. The container may have a depressed bottom to assure the maximum collection of fluids, and the lid may have a recess to accommodate the air-evacuated tube.

7 Claims, 11 Drawing Figures

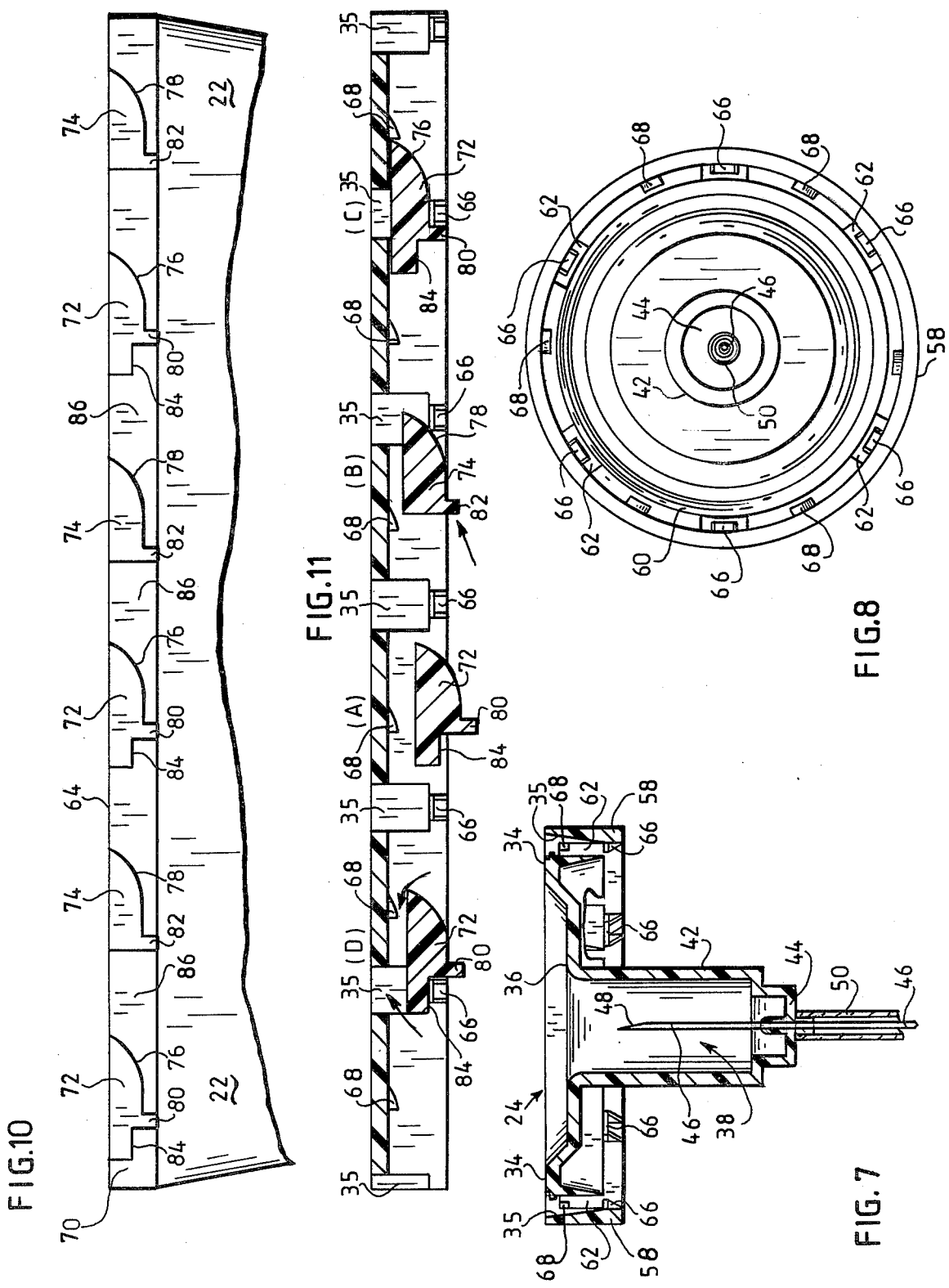

LIQUID SPECIMEN CONTAINER

CROSS-REFERENCE TO RELATED APPLICATION

This application is a continuation-in-part of our co-pending U.S. Patent Application Ser. No. 856,304 filed Dec. 1, 1977 now abandoned.

BACKGROUND OF THE INVENTION

1. Field of the Invention

The invention relates to a cup or container used for collecting urine or other biological liquid specimens after which the lid for the container is replaced and the container sealed by the patient or supervising personnel. An air-evacuated collection container can be used to extract portions of the specimen from the sealed container without removing the lid, thereby dividing the specimen among several other vessels without contaminating the specimen in the container, workers, or the outside of the vessels. The transferring may be done without pouring or pipetting the collected specimen.

2. Summary of the Invention

The invention comprises
a liquid collection container;
a lid adapted to fit over the container; and
a cannula which runs from the lower end of the container up through the lid with its upper end projecting above the lid so as to be able to pierce the stopper of a stoppered, air-evacuated collection tube.

The lid may have a recess for accommodation of the air-evacuated tube and the container may have a depressed bottom to assure the maximum collection of contained fluids.

BRIEF DESCRIPTION OF THE DRAWINGS

FIG. 7 is a cross-sectional, side elevation of the lid component shown in FIG. 5.

FIG. 8 is a view of the underside of the lid component shown in FIG. 7.

FIG. 10 is a view of the rim of the cup component as shown in FIG. 8 but laid out.

FIG. 11 is a laid-out view of the portion of the lid component which mates with and locks to the rim of the cup portion shown in FIG. 10.

DETAILED DESCRIPTION OF THE PREFERRED EMBODIMENTS OF THE INVENTION

Figure 1:
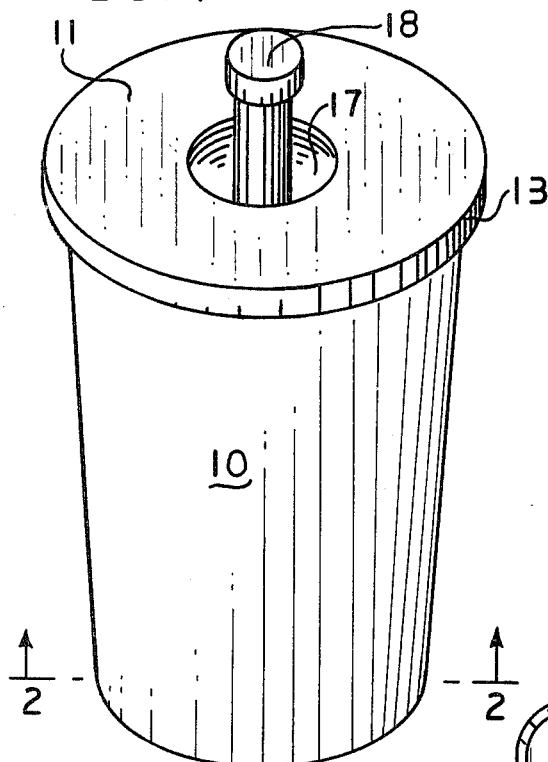
FIG. 1 is an isometric view of the container and lid of an embodiment of the present invention.
Figure 2:
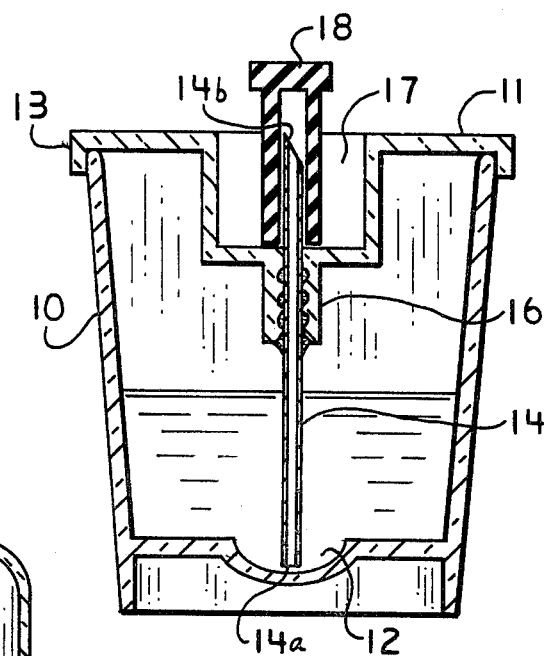
FIG. 2 is a cross-sectional side elevation of the container and lid of FIG. 1.
Figure 3:
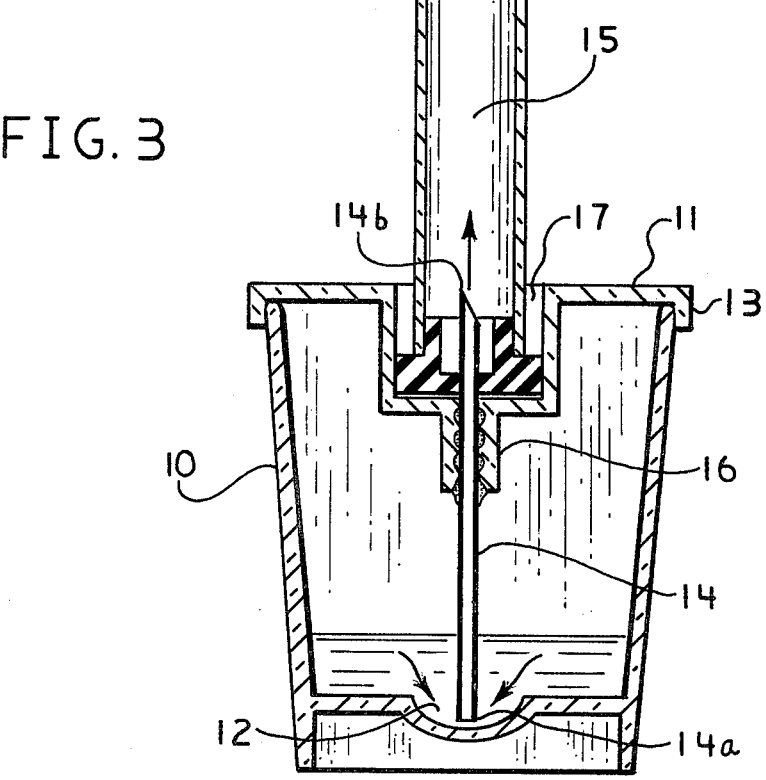
FIG. 3 is a view similar to FIG. 2 with the cap removed from the point of the cannula and an air-evacuated tube forced over the needle point and positioned in the recess of the lid.

Referring to the drawings there is shown in FIGS. 1 and 2 a cup 10 in which urine or other biological liquid specimens may be collected after which the patient or supervising nurse places a lid 11 on the cup. The cup may be provided with a depression 12 in the bottom to assure maximum collection of small volume fluids in the bottom of the cup.

The lid 11 has a flange 13 around its outer rim of a size to provide a tight fit when the lid is placed over the cup 10. The lid has a cannula 14 which passes through the lid with its bottom end 14a extending into the bottom of the cup or into the depression 12 in the bottom of the cup if the cup is provided with such depression. The top end of the cannula projects through the lid so that its needle point 14b is adapted to pierce the stopper 15a of an air-evacuated tube 15 for withdrawing liquid from within the cup. To rigidly secure the cannula in the lid a barrel 16 or similar support projects inwardly from the lid. The lid may be provided with a recess 17, which recess is sufficiently large to receive the end of an air-evacuated tube 15 when the stopper of the tube 15 is pierced by the needle point 14b projecting upward from the bottom of the recess. Such recess 17 serves to position the air-evacuated tube 15 for piercing the needle point. If the recess 17 is omitted, the needle point 14b will project above the flat surface of the lid sufficiently to permit the needle point to pierce the stopper of the tube 15. When no sample is being removed from the specimen in the cup a cap 18 is fitted over the needle point 14b of the cannula to prevent leakage through the cannula.

When a sample of the specimen is to be removed from the cup it is only necessary to place the air-evacuated tube 15 over the needle point 14b so that the needle pierces the stopper 15a of the tube 15. Since it is not necessary to remove the lid 11, no outside contamination of the tube 15 occurs. Furthermore, following shaking or mixing of the specimen, liquid does not run down the outside of the cup as with most specimen cups requiring removal of the lid. If the air-evacuated tube 15 containing either urine preservative or a sputum digestant is placed on the needle, there will be no contamination of the specimen container or tube 15 when it is sent to the laboratory. This method provides a means for reducing the possibility of contaminating the nurse and laboratory worker with infectious agents present in the specimen by eliminating the need for pouring or pipetting portions of the specimen to several containers for processing by various departments in the laboratory.

Those skilled in the art will appreciate that many variations of the above described embodiment of the invention may be made without departing from the spirit and the scope of the invention. For example, referring now to FIG. 4, there is seen a cross-sectional, side elevation of a preferred embodiment collection container 20 of the invention. The container 20 comprises a cup 22 portion and a removable lid 24 portion. The cup 22 comprises a tapering, tubular vessel having continuous, tapered sidewalls 26 separating an open end 28 and a closed end 30. The lid 24 is removably emplaced on the open end 28 of cup 22. The cup 22 with lid 24 together define a collection chamber 32 which is suitable for holding biologically hazardous materials. The cup 22 and lid 24 may be fashioned from any conventional material such as, for example, a polymeric resin. Polymeric resins are well known in the art and include for example polyethylene, polycarbonate, polystyrene and like polymeric resinous materials.

Figure 5:
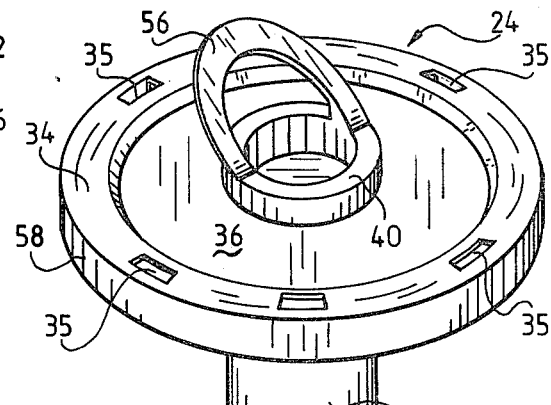
FIG. 5 is an isometric view of the lid component employed in the embodiment container of FIG. 4.
Figure 6:
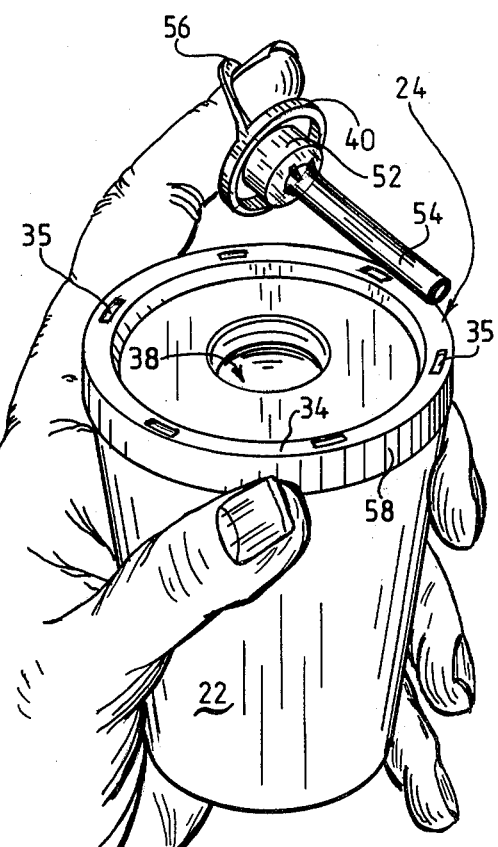
FIG. 6 is a view-in-perspective of the embodiment container of FIG. 4, shown in use.
Figure 4:
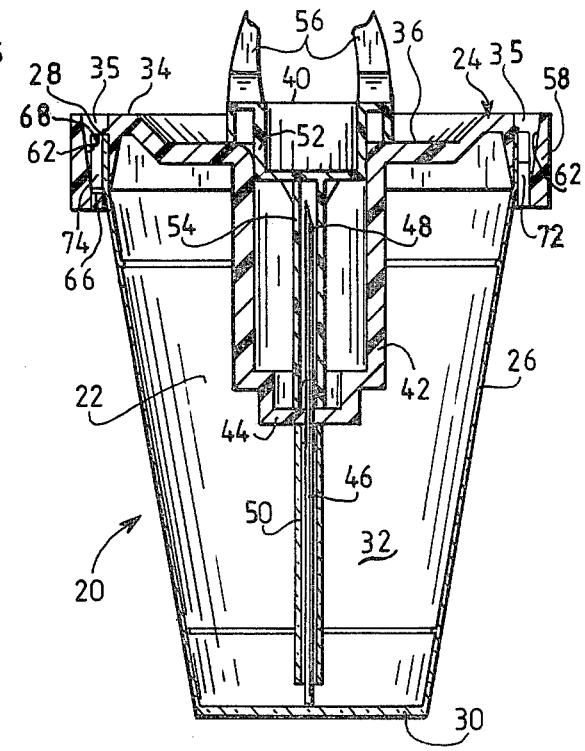
FIG. 4 is a cross-sectional, side elevation of a preferred embodiment container of the invention.

The lid 24 component is shown in an isometric view in FIG. 5 and comprises a generally disc shaped closure member having an outer peripheral portion 34 and an inner zone 36. The outer peripheral zone 34 includes a plurality of spaced aperatures 35 which pierce the outer periphery 34 of lid component 24. Positioned at the central zone 36 is a well 38 (refer briefly to FIG. 6, a view of the cup 22 and lid 24 shown together in perspective view). The well 38 is normally closed with a well cover 40 as shown in FIG. 5. Referring again to FIG. 4, one can see that the centrally located well is formed by sidewalls 42 and an end wall 44 which are continuous with and part of the molded surface of the lid component 24. The well 38 as defined by its sidewalls 42 and end wall 44 projects inwardly into the chamber 32 of cup 22 when lid 24 is emplaced to close the open end 28 of cup 22. Piercing the central portion of end wall 44 is a tubular cannula 46 which is mounted and secured in place, preferably by an epoxy type adhesive. The cannula 46 has a first end positioned adjacent to closed end 30 of cup 22 and a second needle point 48 end which is positioned within the well 38. The cannula is in open communication between chambers 32 and well 38. A cannula sheath guard 50 is secured over the cannula where it is emplaced within chamber 32 as a protection during handling. The well closure member 40, as shown best in FIG. 6, includes a plug portion 52 adapted to close well 38 as shown in FIGS. 4 and 5. On the lower surface of plug 52 is a needle guard 54 which comprises a tubular member adapted to fit over and secure needle point 48 of cannula 46 as shown in FIG. 4. With the closure member 40 in place, not only is the well 38 closed but communication through cannula 46 is prevented by enclosure of the needle point 48 within tubular guard 54. The closure member 40 also includes a finger gripping loop 56 through which an operator may insert a finger to lift and remove the closure member 40 from well 38 as shown in FIG. 6. This structure is particularly advantageous in that it allows for one handed operation as shown in FIG. 6, i.e.; the operator may hold the cup 22 in one hand, insert a finger through loop 56 and by raising the finger remove closure 40 from its emplacement in well 38. This will serve to open communication to the well 38 and the enclosed needle end 48 of cannula 46. With the other hand, the operator may emplace an evacuated tubular container into the well 38 in the same manner previously described in reference to the embodiment container 10. In this way, the operator can conveniently and easily withdraw biologically hazardous materials from chamber 32 into the emplaced evacuated, tubular container. When a sufficient portion of biologically hazardous material has been withdrawn into the evacuated, tubular container from chamber 32, via cannula 46, the operator may remove the emplaced tubular container from well 38 and replace closure member 40, again interrupting communication of cannula 46 from the interior of chamber 32. Those skilled in the art will readily appreciate that the integral, unitary structure of the collection container 20 serves to protect the operator from an unnecessary exposure to potentially hazardous biological materials which may be contained within chamber 32.

Figure 9:
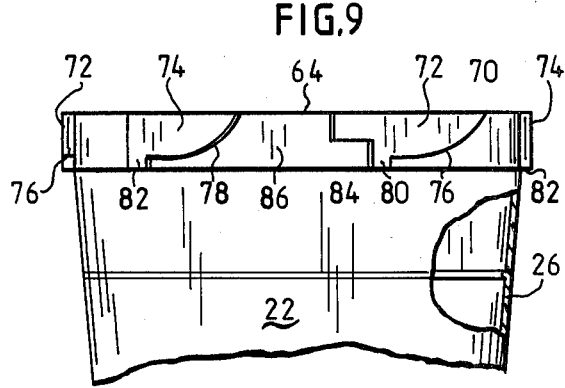
FIG. 9 is a view of the upper end or lip portion of the container of FIG. 4 with the lid removed.

Referring now to FIG. 7, further details of the lid component 24 may be observed. FIG. 7 is a side elevation of lid 24 in cross section, with the closure member 40 removed from well 38. It will be observed in FIG. 7 that a skirt 58 depends downward from peripheral portion 34 of the lid member 24 to partially hide the underside of lid 24. On the inner surface of skirt 58, and periodically placed around the inner aspect of the skirt 58 are locking lugs 66. Spaced inwardly from the inner aspect of skirt 58 is a second or inner skirt 60. The inner skirt 60 together with the inner aspect of outer skirt 58 forms an open ended channel 62 which is adapted by size and configuration to receive the lip 64 (see FIG. 9) of cup 22 at its open end 28. Referring now to FIG. 8, a view of the bottom surface of the lid 24, one can see the relationships of the above described features which also include wedge 68 which is at the closed end of channel 62 adjacent to the inner aspect of outer skirt 58. The function of wedge 68 will be described hereinafter in greater detail. Referring now to FIG. 9, one can see the upper or open end 28 of cup 22 in perspective. Boardering the lip 64 and integrally molded on the outside of the cup 22, is a zone 70 adapted to be received in the previously described channel 62. Integrally molded in raised relief on the zone 70 are locking devices 72, 74. Each of the locking devices 72, 74 includes a caming surface 76, 78 respectively and a stop means 80, 82 respectively. Alternate locking devices 72, 74 also include a stop portion 84 as shown on locking device 72. Referring now to FIG. 10, a laid out view of the rim 64 of the cup component 22 as shown in FIG. 9, one can see the alternating relationship of the locking devices 72, 74. These locking devices serve to bring lid 24 into a sealing relationship with the rim 64 of cup 22 such that there is a fluid seal between lid 24 and cup 22 when the lid 24 is locked in place. Referring now to FIG. 11, the operation of locking mechanism for lid 24 and cup 22 will now be described. FIG. 11 is a laid out view of the portion of the lid component 24 which mates with and locks to the rim 64 of the cup portion 22 shown in FIG. 10. When the lid 24 is placed with rim 64 within channel 62, so that the locking devices 72, 74 are directly beneath aperatures 35, the relationship of locking devices 72, 74 is represented in the zone of FIG. 11 identified with the letter A. Rotating the lid toward the right, the locking devices 72, 74 begin to cam up and over the locking lugs 66 as shown in the zone identified by the capital letter B in FIG. 11. Continuing to rotate the lid toward the right, the locking device 72 or 74 cams fully up and over the locking lug 66 as shown in the zone identified with a capital letter C in FIG. 11. In this fully locked position, the bottom surface 88 of lid 24 is drawn down and in fluid sealed relationship with the rim 64 of cup 22. The lid cannot be removed unless one rotates the lid 24 to the left to decam the locking devices 72, 74 from engagement with locking lugs 66. As also shown in FIG. 11 in the zone identified with the capital letter D, when the lid component 24 is rotated to the left, the locking lugs 66 will engage with the underside of the stop portion 84 on the alternate locking device 72. In this position, the contents of chamber 32 may vent through the loose association of lid 24 with cup 22; however, the lid 22 is prevented from being pulled off cup 22 so that there is no danger of spilling or exposure to the contents of the chamber 32. The wedge 68, when locking devices 72, 74 are fully engaged with locking lugs 66 forces the rim 64 towards the inner skirt 60 to further assure a tight, hermetic, fluid seal between the rim 64 and the components forming channel 62 in the lower side of the lid component 24. This hermetic seal is particularly advantageous for the storage of biologically hazardous material in the chamber 32.

Those skilled in the art will appreciate the simple, unitary construction of the container 20 and the ease with which it may be operated in association with air-evacuated, tubular containers of the type described in conjunction with the container embodiment 10. The protection that the containers 10,20 offer to the operator are evident. There are few loose parts which require separate manipulation for the transfer of contained materials.

We claim:

1. A collection container for collecting, transporting and dispensing a potentially hazardous, biological liquid, which comprises a cup to hold said liquid, said cup having an open end, a closed end and sidewalls joining said ends;

a lid adapted to close the open end, mounted on the open end of the cup and having a central portion, a peripheral margin and a sealing flange at the periphery of the peripheral margin, said peripheral sealing flange making sealing engagement with the open end of the cup, the central portion comprising a continuous, closed recess projecting inwardly inside the cup, said recess having an access portal on the outer surface of said lid and said recess being of a size adapted to receive the cannula pierceable end of a stoppered, air-evacuated tube; and a cannula mounted on the central portion of said lid with a first needle end positioned wholly within the recess in a position to pierce the stopper of an air-evacuated tube when said tube is received with its pierceable stopper end first into said recess, and a second needle end within the cup so that communication between said cup and the tube is established when said tube is inserted in the recess.

2. The container of claim 1 wherein the needle point is covered with a cap to prevent leakage through the cannula when no sample is to be removed from the cup.

3. A collection container for collecting, transporting and dispensing a potentially hazardous, biological liquid, which comprises:

a cup to hold said liquid, said cup having an open end, a closed end and sidewalls joining said ends;

a lid adapted to close the open end, mounted on the open end of the cup and having a central portion, a peripheral margin and a sealing flange at the periphery of the peripheral margin, said peripheral sealing flange making sealing engagement with the open end of the cup, the central portion comprising a continuous, closed recess projecting inwardly of the cup, said recess having an access portal on the outer surface of said lid and said recess being of a size adapted to receive the cannula pierceable end of a stoppered, air-evacuated tube; and a cannula mounted on the central portion of said lid with a first needle end positioned wholly within the recess in a position to pierce the stopper of an air-evacuated tube when said tube is received with its pierceable stopper end first into said recess, and a second needle end within the cup so that communication between said cup and the tube is established when said tube is inserted in the recess, the bottom of the cup being provided with a depression and the second needle end of the cannula extending into such depression to assure maximum collection of the liquid in the bottom of the cup.

4. The container of claim 3 wherein said recess is closed by a removable closure.

5. The container of claim 3 wherein the sealing flange includes a plurality of wedges for forcing the open end of the cup against a skirt, said skirt depending from the peripheral margin of the lid.

6. The container of claim 5 wherein the lid is secured in place on the open end of the cup by a removable locking means.

7. The container of claim 6 wherein said locking means comprises a plurality of locking lugs disposed on the skirt, said lugs being adapted to mate to and lock with raised caming surfaces on the open end of the cup.

* * * * *